United States Patent [19]

Akiyama et al.

[11] 4,413,359

[45] Nov. 8, 1983

[54] IMPERMEABLE LAMINATE MEMBRANE

[75] Inventors: Taichiro Akiyama, Tokyo; Fumio Wada, Tsuruoka, both of Japan

[73] Assignee: Koken Co., Ltd., Tokyo, Japan

[21] Appl. No.: 352,528

[22] Filed: Feb. 26, 1982

[30] Foreign Application Priority Data

Mar. 4, 1981 [JP] Japan ............................ 56-31008

[51] Int. Cl.$^3$ ...................... A61F 1/00; A61F 1/24
[52] U.S. Cl. ............................................. 3/1; 3/36;
128/1 R; 128/DIG. 14; 128/DIG. 21; 428/35;
428/421; 428/422; 428/447; 525/937
[58] Field of Search .............. 428/421, 422, 447, 35;
206/438; 229/55; 128/1 R, DIG. 14, DIG. 21;
3/1, 36; 525/937

[56] References Cited

U.S. PATENT DOCUMENTS

| 3,398,043 | 8/1968 | Youngs | 428/422 |
| 3,686,731 | 8/1972 | Koori | 428/447 |
| 3,967,042 | 6/1976 | Laskin | 428/422 |
| 4,215,178 | 7/1980 | Martin, Jr. | 428/422 |

FOREIGN PATENT DOCUMENTS 29292  5/1981  European Pat. Off. ............ 3/36

OTHER PUBLICATIONS

Robert B. Bergman, "Exudation of Silicone Through the Envelope of Gel-Filled Breast Prosthese: An In Vitro Study," (1979), vol. 32, pp. 31 to 34.

Dr. Yasuo Muto, "Augementation of Mamma Plasty in Japan" to 14th Postgraduate Instructional Course Lecture Manuscript.

Primary Examiner—Ellis P. Robinson
Attorney, Agent, or Firm—Wegner & Bretschneider

[57] ABSTRACT

An impermeable laminated membrane, constructed by the superposition of a silicone rubber membrane on a fluoro-rubber membrane, is disclosed.

This laminated membrane has an extremely low permeability so that its is effective for implantation into living organisms.

3 Claims, 2 Drawing Figures

IMPERMEABLE LAMINATE MEMBRANE

BACKGROUND OF THE INVENTION

1. Field of the Invention

The present invention relates to an impermeable laminate membrane bag having an extremely low permeability, and more particularly, to a laminate membrane bag which is suitable for implantation into living organisms.

2. Brief Description of the Prior Art

Silicones and fluoropolymers were established as medical plastics because of their outstanding compatibility with tissue and stability in living organisms. In particular, silicones are used for extracorporeal circulation circuits, implanted shunt for hemodialysis, catheters, mamma prosthesis, etc., and fluoropolymers are used for trachea cannula, etc. In addition, silicones are used for gas permeation membranes of pump-oxygenators and soft contact lenses, by virtue of their outstanding compatibility with living organisms, stability, and gas permeability.

Flexible and elastic silicone rubber membranes are formed into a baggy implantation material, which is used to fill the voids in the living organisms after such membranes have been filled with silicone gel or physiological saline. Examples of such a use include mamma prosthesis and testis prosthesis. The baggy implantation material which contains a gel or liquid suffers from the disadvantage that its contents, e.g., the silicone gel, may permeate through the membrane into the living organism, causing the connective tissue surrounding the prosthesis to become tylotic, and then shrink. This tissue area has a hard feel, when touched from outside. Therefore, to avoid this undesirable result it is necessary to prevent the silicone filler from leaking through the membrane. If the contents leak through the membrane, the baggy implantation material shrinks in size, losing its initial shape. Thus, if a silicone membrane is to be used for such an implantation material, the permeability of the silicone membrane should be kept low. For instance, in the case of mamma prosthesis, the permeation is reduced by gelling or polymerizing the silicone oil in the silicone rubber membrane bag so as to decrease permeable low-molecular weight silicone. Nevertheless, the residual low-molecular weight silicone permeates over a prolong period of time, leading to the previously discussed problem. An attempt has been made to replace silicone with physiological saline, but water also permeates the membrane and does not permit shape retention. Thus, it has not been possible to prevent the permeation by polymerizing the content of the bag.

OBJECTS AND SUMMARY OF THE INVENTION

An object of the present invention is to provide an impermeable laminate membrane suitable for implantation into living organisms.

Another object of the present invention is to provide an impermeable laminate membrane having an extremely low permeability.

In accordance with an aspect of the present invention, the impermeable laminate membrane comprises a laminate of at least a silicone rubber membrane and a fluororubber membrane.

DETAILED DESCRIPTION OF THE INVENTION

The impermeable silicone rubber in accordance with the present invention is prepared by laminating a silicone rubber membrane with a fluororubber membrane which has almost the same strength and elongation as silicone rubber but does not permit water and low-molecular weight silicone oil to permeate therethrough. The laminate may be of a two-layer structure consisting of one silicone rubber layer and one fluororubber layer or of a three-layer structure in which one fluororubber layer is sandwiched by two silicone rubber layers. In addition, a multilayered structure is also possible in which silicone rubber layers and fluororubber layers are disposed one over another.

The term "silicone elastomer" herein referred to is intended to mean a cured dimethylsiloxane polymer obtained from the three part system silicone elastomer commercially available under the tradename Dow Corning Q7-2245 Silicone Elastomer from the Dow Corning Corporation, which consists of Part A (containing a dimethylsiloxane polymer and reinforcing silica), Part B (a polysiloxane curing agent) and Part C (an additive useful for inhibiting the ambient temperature cure of the mixed Part A and Part B). Recommended conditions for application are indicated in Bulletin 51-362 (August, 1977) issued by the Dow Corning Corporation.

The term "fluororubber" herein referred to means the vinylidene fluroride-hexafluoropropylene-based fluororubber commercially available under the tradename DAI-EL G-501 from Daikin Kogyo Co. Ltd., in Japan, which is, according to a technical bulletin, FLUOROCARBON ELASTOMER, by Daikin Kogyo Co. Ltd., a white to pale yellow block elastomer and has a specific gravity of 1.84 at 25° C. and a mooney viscosity of about 100 ML1+10 (at 100° C.).

According to the above-mentioned laminate structure, the permeation of silicone oil and water is effectively prevented due to the impermeable fluororubber membrane bag. Sufficient impermeability can also be achieved by a two-layer structure in which the external layer is silicone rubber and the internal layer is a fluororubber. The laminate membrane bag of this invention does not delaminate after repeated elongation and contraction because the silicone rubber layer and the fluororubber layer have almost the same strength and elongation. As for delamination, the three-layer structure is superior to the two-layer structure.

EXAMPLE

Figure 1:
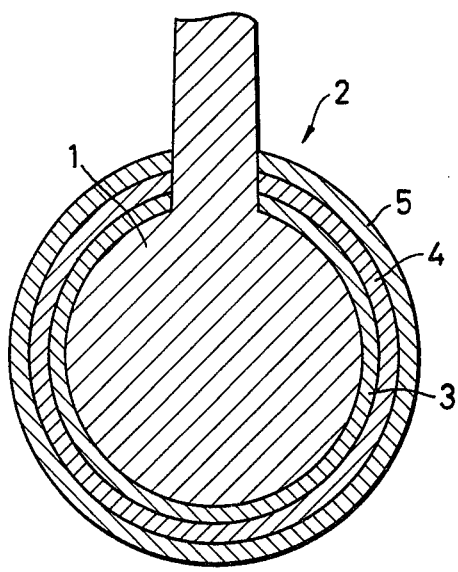
FIG. 1 is a longitudinal sectional view showing the process of preparing the prosthesis in the example of this invention.
Figure 2:
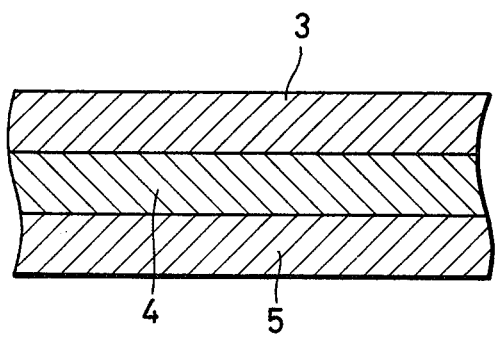
FIG. 2 is an enlarged sectional view of the prosthesis prepared in the example.

A solution having a 15% silicone rubber concentration was prepared by dissolving Dow Corning Q7-2245 Silicone Elastomer (tradename for a three part system silicone product consisting of Parts A, B and C available from the Dow Corning Corp.) in hexane. In this Example 0.7 parts of Part B (polysiloxane curing agent) and 0.32 parts of Part C (additive useful for inhibiting the ambient temperature cure of the mixed Part A and Part B) were used for 100 parts of Part A (dimethylsiloxane polymer and a reinforcing silica). This solution was coated by dipping process to the sphere (1) of the mold (2) and the coated layer was air dried for 30 minutes. This coating-air drying process was repeated three times and the resulting silicone rubber layers (3) was cured at 60° for 1 hour. Then a fluororubber solution was applied to the silicone rubber layer (3). The fluororubber solution was prepared by dissolving DAI-EL G-501 (tradename for vinylidene fluoride-hexafluoropropylene-based fluororubber from the Diakin Kogyo Co. Ltd., Japan) in methyl isobutyl ketone at a concentration of 13%. The coating was air dried and cured at 60° C. for 30 minutes to form a fluororubber layer (4) as shown in FIG. 1. The external silicone rubber layer (5) was formed by coating the silicone rubber solution again on the fluororubber layer (4) in the same manner as the internal silicone rubber layer (3). Thus, the laminate of three-layer structure was obtained as shown in FIGS. 1 and 2 which is made up of the internal silicone layer (3), the intermediate fluororubber layer (4), and the external silicone layer (5). After heat treatment at 60° C. for 4 to 7 hours, preferably 6 hours, the laminate was demolded from the mold (2), followed by additional heat treatment at 150° C. for 30 minutes. The resulting impermeable laminate bag has a thickness of 0.18 to 0.22 mm. The membrane thickness can be adjusted by changing the concentration of the silicone rubber solution and the number of coatings. The thickness of the flurorubber layer should be 0.02 to 0.03 mm to insure impermeability of the laminate membrane.

The bag of the laminate membrane prepared in the above step was sealed after filling a mixture of 30 parts by volume of Dow Corning silicone oil 2150 and 10 parts by volume of Dow Corning silicone oil 2146, followed by heating at 150° C. for 3.5 hours for polymerization of the silicone oils. The contents of the bag become gelled. The silicone prosthesis thus prepared was tested for silicone permeation and mechanical properties. The results are shown in Table 1.

In the comparative example, the membrane has the same thickness as the laminate membrane of the example but has no fluororubber layer.

TABLE 1

|  | Example of Present Invention | Comparative Example |
| --- | --- | --- |
| Silicone oil permeability, mg/cm$^2$/month | 0.84 | 2.05 |
| Tensile strength, kg/cm$^2$ | 83 | 73 |
| Tear strength, kg/cm | 18.4 | 22.7 |
| Elongation, % | 620 | 625 |

As shown in Table 1, the prosthesis prepared in the example has very little silicone permeability and yet has almost the same mechanical strength, such as tensile strength and elongation, as the comparative example. In other words, the laminate obtained in this example has superior properties for mamma prosthesis and testis prosthesis. It was also found that the laminate membrane obtained in this example is effective to prevent permeation of water. This was confirmed by measuring the change of weight due to water permeation and evaporation while the membrane bag filled with physiological saline in place of silicone was allowed to stand at room temperature for a long period of time. This result suggests that the laminate membrane of this invention would be also useful for prosthesis containing physiological saline in lieu of silicone oil.

Although the invention has been described with reference to the example, it is to be understood that the invention is not limited to the specific embodiment, but modification and variation of the invention are possible without departing from the spirit and scope thereof. Owing to its ability to prevent a gas from permeating, the laminate membrane will find application for the balloon-like cuff which is filled with air when in use. A cuff made of the laminate membrane of this invention will keep its shape for a long time with less frequent replenishment of air, because the leakage of air through the membrane is extremely reduced.

What is claimed is:

1. An implantable impermeable laminate membrane bag for use in living organisms comprising a laminate of at least one membrane of a cured dimethylsiloxane polymer and at least one membrane of a vinylidene fluoride-hexafluoropropylene-based fluororubber.

2. The impermeable laminate membrane bag according to claim 1, further comprising an additional membrane of the cured dimethylsiloxane polymer.

3. The impermeable laminate membrane bag according to claim 1 or 2 wherein the membrane of the vinylidene fluoride-hexafluoropropylene-based fluororubber is interposed between the two membranes of the cured dimethylsiloxane polymer.

* * * * *